(12) United States Patent
Thornton et al.

(10) Patent No.: US 9,133,412 B2
(45) Date of Patent: Sep. 15, 2015

(54) ACTIVATED GASEOUS SPECIES FOR IMPROVED LUBRICATION

(71) Applicants: Jackson Thornton, Raleigh, NC (US);
Vinay G. Sakhrani, Raleigh, NC (US);
Charles Tomasino, Raleigh, NC (US);
Robert A. Mineo, Raleigh, NC (US)

(72) Inventors: Jackson Thornton, Raleigh, NC (US);
Vinay G. Sakhrani, Raleigh, NC (US);
Charles Tomasino, Raleigh, NC (US);
Robert A. Mineo, Raleigh, NC (US)

(73) Assignee: TriboFilm Research, Inc., Raleigh, NC (US)

( * ) Notice: Subject to any disclaimer, the term of this patent is extended or adjusted under 35 U.S.C. 154(b) by 216 days.

(21) Appl. No.: 13/833,707

(22) Filed: Mar. 15, 2013

(65) Prior Publication Data

US 2014/0011717 A1    Jan. 9, 2014

Related U.S. Application Data

(60) Provisional application No. 61/669,623, filed on Jul. 9, 2012.

(51) Int. Cl.
| | | |
|---|---|---|
| *C23C 16/56* | (2006.01) | |
| *C10M 147/04* | (2006.01) | |
| *C10M 155/02* | (2006.01) | |
| *C10M 177/00* | (2006.01) | |

(52) U.S. Cl.
CPC ........... *C10M 155/02* (2013.01); *C10M 147/04* (2013.01); *C10M 177/00* (2013.01); *C10M 2213/0606* (2013.01); *C10M 2229/0405* (2013.01); *C10M 2229/0415* (2013.01); *C10N 2230/06* (2013.01); *C10N 2240/66* (2013.01); *C10N 2280/00* (2013.01)

(58) Field of Classification Search
CPC .............................. C23C 16/56; C10M 147/04
USPC .................. 427/2.3, 2.28, 533, 536, 535, 569
See application file for complete search history.

(56) References Cited

U.S. PATENT DOCUMENTS

| | | |
|---|---|---|
| 4,020,046 A | 4/1977 | King et al. |
| 4,088,926 A | 5/1978 | Fletcher et al. |
| 4,368,313 A | 1/1983 | Hayes |

(Continued)

FOREIGN PATENT DOCUMENTS

| | | |
|---|---|---|
| GB | 1357113 | 6/1974 |
| GB | 1417239 | 12/1975 |

(Continued)

OTHER PUBLICATIONS

S. Crystal Coley et al., "Performance of three portable infusion-pump devices set to deliver 2 ml/hr", Am. Jrnl. of Health-System Pharmacists, vol. 54, Jun. 1, 1997, pp. 1277-1280.

(Continued)

*Primary Examiner* — Cachet Sellman
(74) *Attorney, Agent, or Firm* — The Law Office of David P. Hendricks

(57) ABSTRACT

The present application is directed to methods and devices for altering material properties of lubricants and other cross-linkable compounds comprising organic or organometallic materials through exposure to energized gaseous species. The energized gaseous species may create reactive sites among lubricant molecules that may alter their material properties by cross-linking at least a portion of the lubricant molecules. The cross-linked lubricant may reduce the ability of the lubricant to migrate away when force is applied between lubricated sliding friction surfaces.

49 Claims, 7 Drawing Sheets

(56) References Cited

U.S. PATENT DOCUMENTS

| | | | |
|---|---|---|---|
| 4,536,179 A | 8/1985 | Anderson et al. | |
| 4,688,935 A | 8/1987 | Barnes et al. | |
| 4,767,414 A | 8/1988 | Williams et al. | |
| 4,822,632 A | 4/1989 | Williams et al. | |
| 4,842,889 A | 6/1989 | Hu et al. | |
| 4,844,986 A | 7/1989 | Karakelle et al. | |
| 4,960,609 A | 10/1990 | Homola et al. | |
| 5,037,668 A | 8/1991 | Nagy | |
| 5,041,304 A | 8/1991 | Kusano et al. | |
| 5,225,659 A | 7/1993 | Kusano | |
| 5,331,487 A | 7/1994 | Gregory et al. | |
| 5,338,312 A | 8/1994 | Montgomery | |
| 5,409,738 A | 4/1995 | Matsunuma et al. | |
| 5,591,481 A | 1/1997 | Takahashi et al. | |
| 5,733,610 A | 3/1998 | Okazaki et al. | |
| 5,830,577 A | 11/1998 | Murayama et al. | |
| 5,958,544 A | 9/1999 | Usuki | |
| 6,090,081 A | 7/2000 | Sudo et al. | |
| 6,200,627 B1 | 3/2001 | Lubrecht | |
| 6,221,434 B1 | 4/2001 | Visca et al. | |
| 6,558,889 B1 | 5/2003 | Oishi et al. | |
| 6,613,394 B2 | 9/2003 | Kuckertz et al. | |
| 6,835,278 B2 | 12/2004 | Selbrede et al. | |
| 7,431,989 B2 | 10/2008 | Sakhrani et al. | |
| 7,553,529 B2 | 6/2009 | Sakhrani et al. | |
| 7,674,504 B2 | 3/2010 | Sakhrani et al. | |
| 8,084,103 B2 | 12/2011 | Sakhrani et al. | |
| 8,124,207 B2 | 2/2012 | Sakhrani et al. | |
| 2002/0037653 A1 | 3/2002 | Herchen | |
| 2002/0192385 A1 | 12/2002 | Jenkner et al. | |
| 2005/0031876 A1 | 2/2005 | Lu | |
| 2008/0038484 A1 | 2/2008 | Alcott et al. | |
| 2008/0145565 A1 | 6/2008 | Sakhrani | |
| 2009/0126404 A1* | 5/2009 | Sakhrani et al. | 65/30.1 |
| 2010/0273315 A1* | 10/2010 | Ovshinsky | 438/478 |

FOREIGN PATENT DOCUMENTS

| | | |
|---|---|---|
| JP | 05-140573 | 6/1993 |
| JP | 06-304243 | 11/1994 |
| JP | 11-342371 | 12/1999 |
| JP | 2000-057564 | 2/2000 |
| JP | 2004-510571 | 4/2002 |
| JP | 2002-224735 | 8/2002 |
| WO | 03/080258 | 10/2003 |

OTHER PUBLICATIONS

T. Neff, et al., "Evaluation of the FASTSTART mode for reducing start-up delay in syringe pump infusion systems", Swiss Medical Weekly, vol. 131, 2001, pp. 219-222.

R. Ferrari and D.R. Beech, "Infusion Pumps: guidelines and pitfalls", Australian Provider, vol. 18, No. 2, 1995.

Jody L. Carl et al., "Fluid delivery from infusion-pump syringes", Am. Jrnl. Of Health-System Pharmacists, vol. 52, Jul. 1, 1995, pp. 1428-1432.

A. Leibmann-Vinson, et al., "Physics of Friction in Disposable Plastic Syringes", The American Physics Society meeting, Mar. 1997, Session J32.02.

K.Y. Byun, et al., "Effect of Free Radicl Activation for Low Temperature Si to Si Wafer Bonding", Journal of the Electrochemical Society, vol. 157, 2010, pp. H109-H112.

T. Harada et al., "Evaluation of corrosion resistance of SiCN-coated metals deposited on an NH3-radical-treated substrate", Thin Solid Films, vol. 519, 2011, pp. 4487-4490.

Y.W. Parl et al., "A New Approach for Selective Surface Modification of Fluoropolymers by Remote Plasma", Journal of Applied Polymer Science, vol. 93, 2004, pp. 1012-1020.

R.E. Belford et al., "Surface activation using remote plasma for silicon to quartz wafer bonding", Microsystem Technology, vol. 15, 2009, pp. 407-412.

N. Inagaki et al., "Surface Modification of Aromatic Polyamide Film by Remote Oxygen Plasma", Journal of Applied Polymer Science, vol. 64, 1997, pp. 831-840.

Y. Tamada et al., "Surface Modification of Poly(tetrafluoroethylene) by Remote Hydrogen Plasma", vol. 29, 1996. pp. 4331-4339.

K. Hashimoto et al., "Systematic study on photoresist removal using hydrogen atoms generated on heated catalyzer", This Solid Films, vol. 501, 1996, pp. 326-328.

M. Akahori, "A New Test Method for Weatherability Prediction: Radical Shower Using a Remote Plasma Reactor", Surface Coatings International Part B: Coatings Transactions, vol. 89, No. 2, Jun. 2006, pp. 163-168(6).

* cited by examiner

ACTIVATED GASEOUS SPECIES FOR IMPROVED LUBRICATION

CROSS-REFERENCE TO RELATED APPLICATIONS

The present application claims priority to provisional U.S. Patent Application Ser. No. 61/669,623, filed on Jul. 9, 2012, titled "Activated Gaseous Species for Improved Lubrication," which is hereby incorporated by reference in its entirety.

FIELD OF THE INVENTION

The present invention is directed generally to systems and methods for treating a surface, and more specifically to treat a substance applied to the surface by exposing the substance to energized gaseous species.

BACKGROUND

In order to minimize the frictional forces between two surfaces, a lubricant is applied to the surface to reduce the force required to initiate and maintain sliding movement. However, when two lubricated surfaces remain in contact for prolonged periods of time, the lubricant has a tendency to migrate away from the area of contact due to the compressive force between the two surfaces. This effect will increase as the compressive force increases. As more lubricant migrates away from between the two surfaces, the force required to initiate movement will increase and can revert back to that of the non-lubricated surfaces causing stiction to occur. This phenomenon can also occur in slow moving systems. Because of the slow speed, the time interval is sufficient to cause the lubricant to migrate away from the area of contact resulting in a high movement force. Once the object moves past the lubricant-depleted area, the sliding object returns in contact with the lubricant-rich area reducing the frictional force, causing a sudden and rapid movement of the sliding object. This phenomenon is referred to as stiction.

SUMMARY

The present application is directed to methods and devices for altering material properties of lubricants and other cross-linkable compounds comprising organic or organometallic materials through exposure to energized gaseous species. The energized gaseous species may create reactive sites among lubricant molecules that may alter their material properties by cross-linking at least a portion of the lubricant molecules. The cross-linked lubricant may reduce the ability of the lubricant to migrate away when force is applied between lubricated sliding friction surfaces.

DETAILED DESCRIPTION

Figure 1:
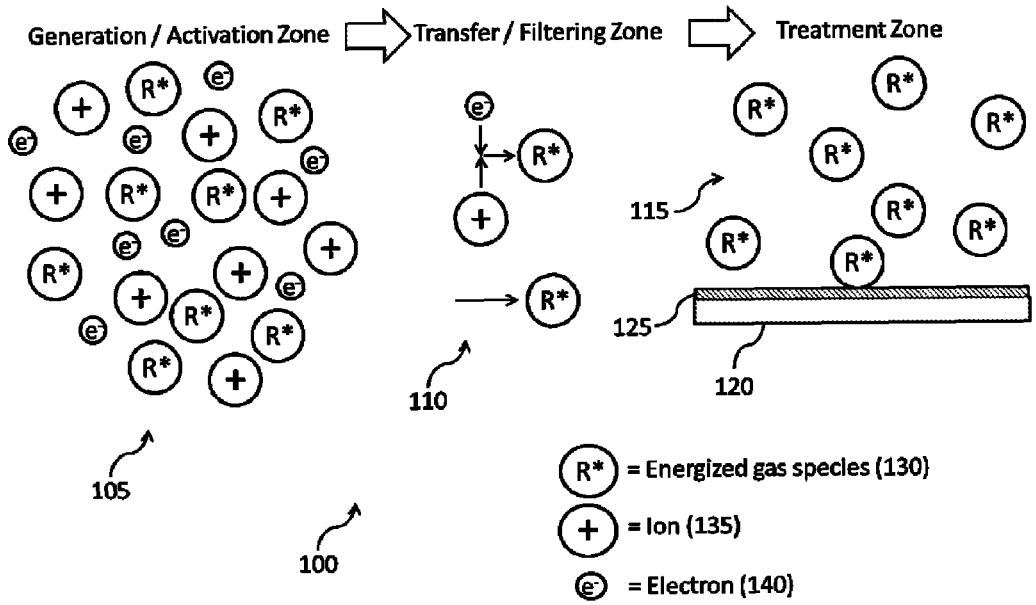
FIG. 1 is a schematic diagram of a method to treat a lubricated surface comprising electron-ion recombination according to various embodiments.

The present application is directed to methods and devices for altering material properties of lubricants comprising organic or organometallic materials through exposure to energized gaseous species (which may also be known as activated gaseous species). The energized gaseous species may create reactive sites among lubricant molecules that may alter their material properties by creating partial cross-links (i.e., cross-linking only a portion of the lubricant molecules available for cross-linking). These partial cross-links may reduce the ability of the lubricant to migrate away when force is applied between lubricated sliding friction surfaces.

The degree of cross-linking may influence the property of the materials to serve as a lubricant. Too little cross-linking may not reduce the tendency of the lubricant to be displaced when subjected to a shear force. Too much cross-linking may affect the lubricious properties of the material. In various embodiments, the degree of cross-linking may be measured as a percentage of the available cross-linkable molecules (on a molar, mass, or volume basis for example), a depth in which cross-linking occurs measured from a top surface of the lubricant, a density (such as moles of cross-links per unit volume), or any other method known in the art.

Energized gaseous species may be created by the bombardment of the gaseous molecules with high energy particles that cause radicalization, ionization, fragmentation, and subsequent recombination of the gaseous molecules. These energized gaseous species may be highly energetic neutrals and/or free radicals. The generation of energized gaseous species may, but not necessarily, coincidentally generate charged species such as ions and electrons. When striking a surface, thermal and electronic energy may be released locally by the energized gaseous species creating reaction sites among the lubricant molecules, nearly instantaneously or through a continued reaction process, which may produce desirable material properties. The reactions that occur and the effects of these reactions on the material properties of the lubricant may depend on the specific energized gaseous species allowed to come in contact with the lubricant.

In contrast, direct ionizing radiation and/or plasma radiation processes may cause retained embedded charges at or near the surface of the lubricant. Retained embedded charges are electrical charges within a material that may result from protonation, deprotonation, adsorption of ions, dissociation of lubricant molecules, or exposure to an electric field. These embedded charges may damage or contaminate the lubricant or the surface underlying the lubricant. Additionally, the damaged surface may lead to further particulate contamination, which may be detrimental to materials in contact with the damaged surface. In medical applications, charge and particle contamination may lead to undesired chemical reactions or direct contamination of medicaments in contact with the surface. Liquid medicants typically contain ions, and these ions may react with the embedded charges. Additionally, the particle contamination may be released from the surface of the lubricant into the medicant.

Excessive direct ionization exposures may cause the lubricant molecules to over cross-link which may render the lubricant useless. However, the lower energy free radicals and excited atoms may have less of a tendency to excessively alter the material properties of the lubricant by over-crosslinking the lubricant molecules or to damage or contaminate the underlying substrate. In quantum mechanics an excited state of a system (such as an atom, molecule or nucleus) is any quantum state of the system that has a higher energy than the ground state. The ground state being the energy of the system in its relaxed state.

There are numerous methods for creating energized gaseous species known in the art. Three such exemplary methods comprise remote plasma generation where the energized gaseous species are generated in the plasma generation zone and then interact with the lubricant downstream from the plasma generation zone; or through generation of energized gaseous species on a catalytic surface, such as a heated wire; or through intense photonic excitation. In the remote gas plasma process, the treatment zone is physically removed from the plasma generation or activation zone. The lubricant which resides in the treatment zone is typically not subjected to charged species such as electrons and ions generated in the plasma generation zone. These charged species may dissipate in processes (either naturally occurring or forced) of electron-positive ion recombination and atom recombination before traveling the distance between the plasma generation zone and the lubricant treatment zone, while the radicals may possess longer lifetimes and may diffuse downstream from the plasma generation zone to the treatment zone and react with the lubricant. In the case of energized gaseous species generation on a catalytic surface, such as a heated wire, thermal energy may be used to energize the gas, which may then diffuse to, or be directed to, the location of the lubricant where cross-linking may take place.

FIG. 1 illustrates a method 100 for creating a gas stream comprising an increased concentration of energized gaseous species 130. The method 100 may comprise filtering by electron-ion recombination according to various embodiments. Species such as electrons 140, ions 135, and energized gaseous species 130 may be formed in a generation/activation zone 105. These various species 130, 135, 140 may then move through a transfer/filtering zone 110 where the species 130, 135, 140 are moved apart from the generation/activation zone 105. A filtering process may occur within the transfer/filtering zone 110 may allow or cause electrons 140 and ions 135 to combine, thereby forming, for example, neutral atoms (or molecules) or additional energized gaseous species 130. The filtering process may then separate at least a portion of the energized gaseous species 130 from any remaining charged species 135, 140. At least a portion of the filtered energized gaseous species 130 may then move to a treatment zone 115 in proximity to a surface 120 which may be at least partially coated with a lubricant 125.

Figure 2:
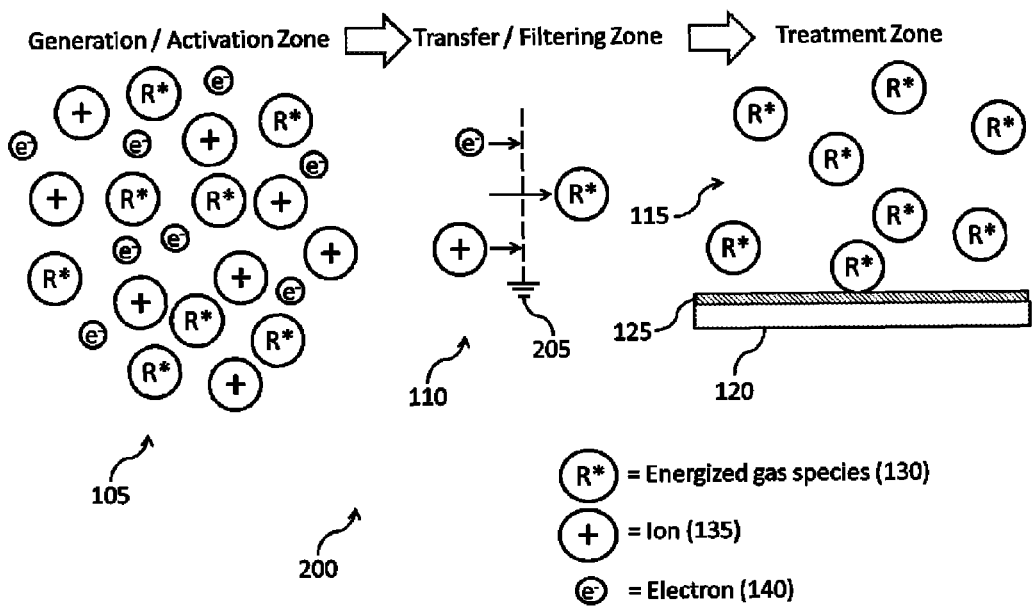
FIG. 2 is a schematic diagram of a method to treat a lubricated surface comprising electrical grounding according to various embodiments.
Figure 3:
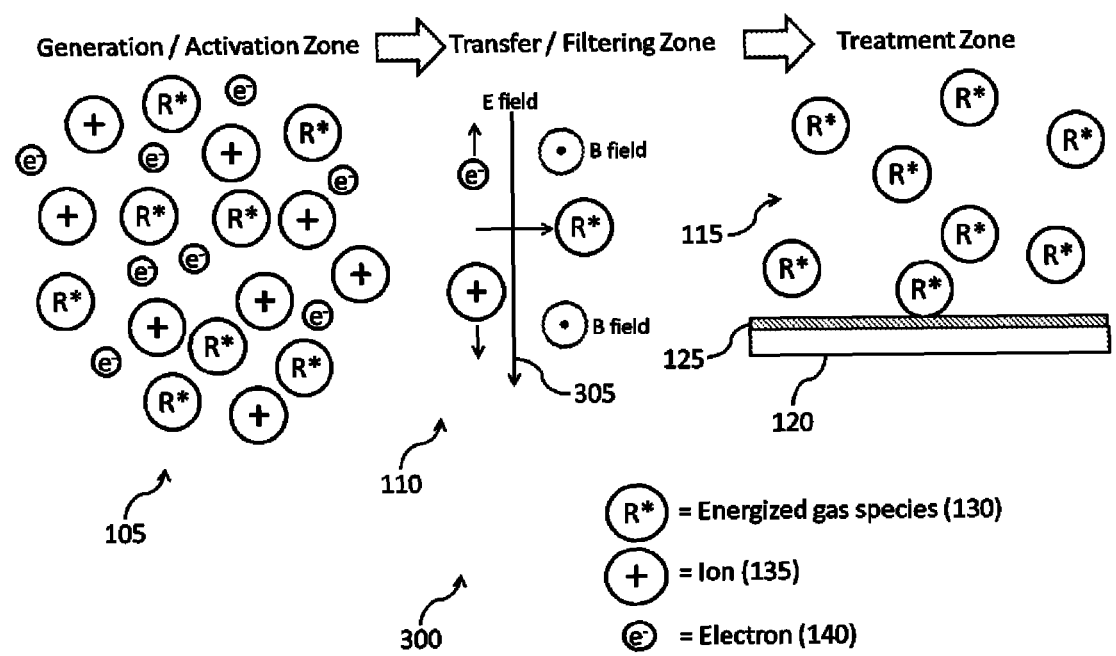
FIG. 3 is a schematic diagram of a method to treat a lubricated surface comprising electrostatic or electromagnetic fields according to various embodiments.

Note that in FIGS. 1 through 3, a symbol of a "+" sign in a circle is used to indicate ions 135 in the gas stream. The "+" is intended to indicate that the molecule or particle has a charge, which may be positive or negative. The use of the "+" sign is not intended to be limiting in any way to only positive ions 135.

Similarly, FIG. 2 illustrates various embodiments of a method 200 for creating a gas stream comprising an increased concentration of energized gaseous species 130. The method 200 may comprise filtering by electrical grounding according to various embodiments. In this example, an electrical ground 205 may be provided which may attract ions 135, electrons 140, and other charged species, thereby filtering the charged species 135, 140 from the energized gaseous species 130. The electrical ground may comprise one or more wires, a screen, a mesh, or any other structure known in the art that is electrically conductive and may be electrically grounded.

FIG. 3 illustrates yet another embodiment of a method 300 for creating a gas stream comprising an increased concentration of energized gaseous species 130. The method 300 may comprise one or more electrostatic or electromagnetic fields 305 to filter ions 135, electrons 140, and other charged species from the energized gaseous species 130. An electrostatic field 305 may generally be described as an area surrounding an electrically charged particle in which the particle may exert an electrical force on other charged particles. If the charged particle has an excess of electrons relative to its surroundings, then the particle will generate a negatively charged electrostatic field 305 that may primarily be exerted on other particles that are positively charged. Conversely, if the charged particle has a deficiency of electrons relative to its surroundings, then the particle will generate a positively charged electrostatic field 305 that may primarily be exerted on other particles that are negatively charged. In an electrostatic field 305, the particles are generally stationary. Electromagnetic fields 305, while functioning similarly to electrostatic fields 305, are produced when charged particles, such as electrons 140, are accelerated.

Both electrostatic fields and electromagnetic fields 305 may produce either a positively or negatively charged field. In the context of the method 300 illustrated in FIG. 3, a positively charged field may be used to repel positively charged species and attract negatively charged species, and a negatively charged field may be used to repel negatively charged species and attract positively charged species. Thus, one or more negatively and positively charged electrostatic and electromagnetic fields 305 may be used to selectively filter positively and negatively charged species from the gas stream. For example, multiple electrostatic and electromagnetic fields 305 with different intensities may be used in series. The first electrostatic and magnetic fields 305 may have lower intensities to separate species having a low charge or low mass from the gas stream. Subsequent electrostatic and electromagnetic fields 305 may have higher intensities to gradually separate species having higher charge or mass from the gas stream.

Methods for producing species such as energized gaseous species 130 (including free radicals), and charged particles such as ions 135 and electrons 140 vary but each method generally produces similar species from a given composition of the gas stream. In various embodiments microwave energy may be used to energize the gas stream. Additionally, a plasma generated using a high-voltage direct current (DC) or radio frequency (RF) power supply may be used to energize the gas stream. The plasma may be generated in a chamber under vacuum (generally less than about 200 torr) or at about atmospheric pressure (generally about 760 torr). In various embodiments, an energized gas stream may be generated by a thermal activation process, such as passing a gas over a catalytic surface or a heated wire.

For plasma processes, a variety of terms such as downstream plasma, remote plasma, non-ionizing radiation zone, and even "quiet plasma" have been given to the region outside of the plasma generation zone. All these terms recognize that the plasma generating zone is different than the remote treatment zone 115. In various embodiments, the energized gaseous species 130 may retain enough energy away from the plasma generating zone (i.e., the generation/activation zone 105) to promote reactions at the surface 120 under conditions that may be more easily controlled to change the material properties of the lubricant 125 and not unduly affect its lubricating properties. Various embodiments may produce energized gaseous species 130 having a lifetime of sufficient length to diffuse (whether by natural processes or induced processes) from the plasma generating zone 105 to the lubricant 125 and retain sufficient energy to influence reaction chemistries of the lubricant 125.

Various embodiments may comprise a lubricant 125 applied to one or more surfaces 120, and then a surface of the lubricant 125 may be exposed to a region (e.g., the treatment zone 115) containing energized gaseous species 130. The energized gaseous species 130 may be generated in a region apart from the lubricated surface 120 (e.g., the generation/activation zone 105) and then transported to the lubricated surface 120. This exposure to the energized gaseous species 130 may alter the physical properties of the lubricant 125 to cause reduced migration of the lubricant 125 when the lubricated surface 120 is in contact with one or more other surfaces by minimizing stiction.

In various embodiments, the physical properties of the lubricant 125 may be altered by cross-linking the molecules of the lubricant 125. Certain physical properties may be obtained (or avoided) by controlling the amount of cross-linking that occurs in the lubricant 125. For example, the amount of cross-linking may be determined by an amount of time the lubricant 125 is exposed to the energized gaseous species 130, a flow rate of the energized gaseous species 130, a chemical composition of the energized gaseous species 130, an amount of energy carried by the energized gaseous species 130, and the like.

Figure 4:
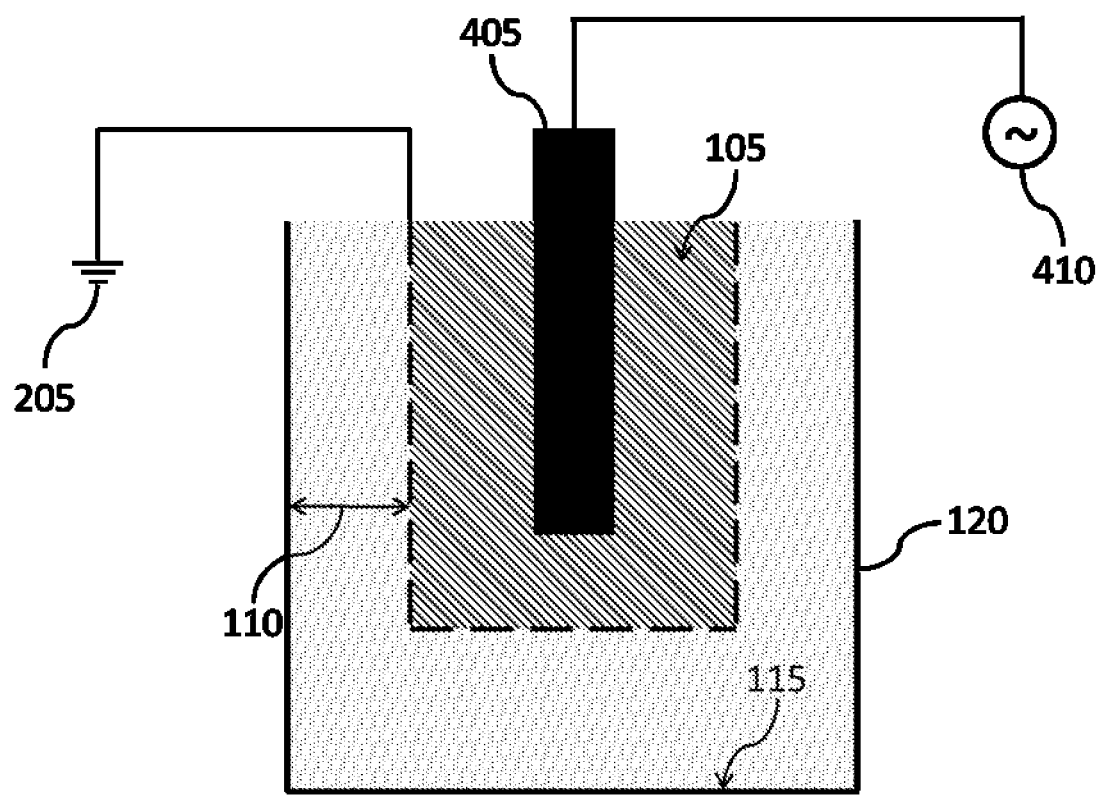
FIG. 4 is a schematic diagram of a device to treat a lubricated surface according to various embodiments.

In various embodiments as illustrated in FIG. 4, the generation/activation zone 105, the transfer/filtering zone 110, and the treatment zone 115 may all be located at least partially within an article comprising the surface 120 to be treated. For example, an electrode 405 coupled to a power supply 410 may be placed at least partially within an area bounded by one or more side walls of the article, at a portion of the side walls comprising the surface 120 to be treated. In various embodiments, the treatment zone 115 and the surface 120 to be treated may be the same. A gas stream may be introduced in proximity to the electrode 405, and an electrical field created by the electrode 405 may cause at least a portion of the molecules of the gas stream to dissociate into charged particles (e.g., ions 135 and electrons 140) and energized gaseous species 130. A filtering device, such as a grounded screen 205, may be placed between the electrode 405 and the surface 120 of the side walls of the article. The filtering device 205 may filter out at least a portion of the charged particles 135, 140, allowing primarily the energized gaseous species 130 to enter the transfer/filtering zone 110. The energized gaseous species may then be transported, such as by inertia due to the flow of the gas stream, to the treatment zone 115 in proximity to the surface 120 of the side walls of the article to be treated.

Figure 5:
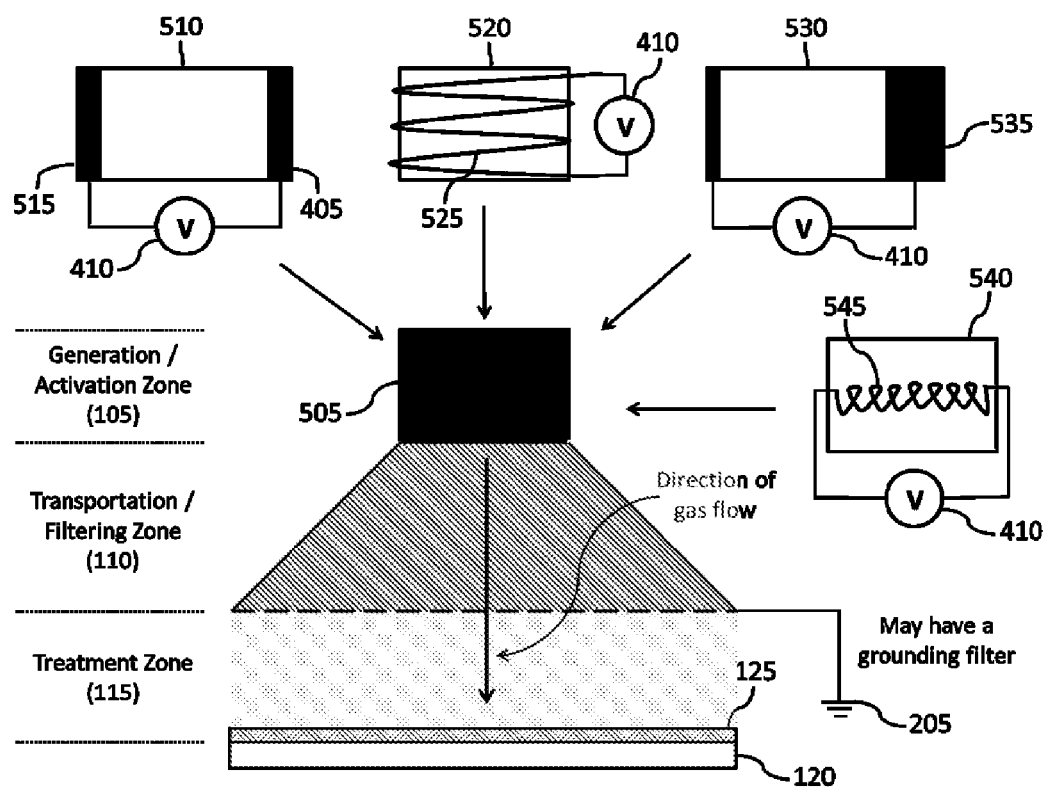
FIG. 5 is a schematic diagram of a device to treat a lubricated surface according to various embodiments.

In various embodiments as illustrated in FIG. 5, a plasma generating device (or other device to generate energized gaseous species as described above), may be located within a chamber 505. Non-limiting examples of plasma generating devices are described as follows. The plasma generating device may comprise a capacitively coupled plasma generating device 510 having two counter electrodes 515 and 405 which are at an electrical potential from each other and are electrically coupled to a power supply 410. The plasma generating device may comprise an inductively coupled plasma generating device 520 having a coil 525 encircling the gas stream. The coil 525 may be electrically coupled to a power supply 410 such that when an alternating electric current is passed through the coil, the inductively coupled plasma is generated and the gas stream is energized. Plasma may also be generated by a microwave plasma generating device 530 in which a microwave generator 535 electrically coupled to a power supply 410 produces electromagnetic radiation that energizes the gas stream. As an example of a non-plasma device for generating activated gaseous species 130, a catalyzer 540 may comprise a wire 545 or other electrically resistive material coupled to a power supply 410. When an electric current is passed through the wire 545, the temperature of the wire 545 increases until the wire 545 is capable of transferring enough energy to the gas molecules to generate energized gaseous species 130. In addition, a plasma generating device (not shown in FIG. 5) could consist of an intense photonic source, such as a flash lamp which generates either visible or UV radiation.

One or more gases may be passed through the chamber 505 coupled to the plasma generating device. A high voltage potential may cause at least a portion of the gas molecules to dissociate into high energy particles. The high energy particles may comprise free radicals, energized gaseous species 130, electrons 140, ions 135, and energetic photons. At least a portion of the electrons 140, ions 135, and other charged species may react with one another or be separated from the energized gaseous species 130 by one or more electrostatic fields, electromagnetic fields, grounding device 205 or other filtration/separation processes and devices. The retained energized gaseous species 130 may then be directed to the lubricated surface 130, which may be located within or outside the chamber 505. The chamber 505 may be held at near atmospheric pressure or at some level of vacuum during generation of the plasma, as described previously.

The various species generated in the generation/activation zone 105 may be separated from the generation/activation zone 105 by diffusion or due to the translational energy of the gas stream due to the flow of the gas. Once the energized gaseous species 130 and other species move a distance from the electrode 405, power source 410, or other device that energizes the gaseous molecules, the energized gaseous species 130 may no longer be influenced by the power source 410 and may continue losing energy through collisions with neutral gas molecules or surfaces 120 such as the lubricant 125. This process may comprise a plasma torch or flame plasma where outside of the plasma zone, the energized gaseous species 130 exists and may be purposely directed to a surface 120.

In various embodiments, the lubricant 125 may comprise a silicone, a fluorochemical compound, a hydrocarbon, or mixtures thereof. The fluorochemical compound may comprise a perfluoropolyether (PFPE). Representative examples of commercially available PFPE include Fomblin M®, Fomblin Y®, and Fomblin Z® families of lubricants from Solvay Solexis; Krytox® from E.I. du Pont de Nemours and Company; and Demnum® from Daikin Industries, Limited. In various embodiments, the lubricant may comprise a functionalized PFPE. Representative examples of commercially available functionalized PFPE include Fomblin ZDOL®, Fomblin ZDOL TXS®, Fomblin ZDIAC®, Fluorolink A10®, Fluorolink C®, Fluorolink D®, Fluorolink E®, Fluorolink E10®, Fluorolink F10®, Fluorolink L®, Fluorolink L10®, Fluorolink S10®, Fluorolink T®, and Fluorolink T10®, from Solvay Solexis. The functionalized PFPE may be an emulsion. Representative examples of commercially available functionalized PFPE emulsions include Fomblin FE-20C® and Fomblin FE-20AG® from Solvay Solexis. In various embodiments, the fluorochemical compound may be a chlorotrifluoroethylene, such as Daifloil® from Daikin Industries, Limited. The silicone may comprise a polysiloxane-based compound in various embodiments, such as a silicone oil with a dimethlypolysiloxane chemical formulation. Additionally, the lubricant 125 may comprise functionalized PFPEs or functionalized polysiloxanes.

The lubricants 125 described above may not, in general, be considered cross-linkable as understood in traditional polymer chemistry. However, the high energy content of the energized gaseous species 130 may contain sufficient energy to overcome the bond strength of the lubricant molecules and initiate one or more chemical reactions by bond cleavage and bond propagation to form a cross-linked lubricant network. These reactions may also create active functional groups that allow hydrogen bonding between functional groups of different lubricant molecules, allowing the molecules to cross-link. Thus, the methods and devices described herein may render the lubricant molecules cross-linkable.

The gas stream may comprise one or more gases selected to generate desired energized gaseous species 130. The gases may also be selected for their propensity not to generate undesired charged species. The gas may be a noble gas including, for example, helium, neon, argon, and krypton. Alternatively, the gas may be an oxidative gas including, for example, air, oxygen, carbon dioxide, carbon monoxide, water vapor, and mixtures thereof. Additionally, the gas may be a non-oxidative gas including, for example, nitrogen and hydrogen. Mixtures of any of these gases may also be used.

The surface 120 may comprise any polymeric, metallic, or ceramic (e.g., glass) material. For example, polymer surfaces 120 may comprise a cyclic olefin polymer, a cyclic olefin copolymer, a polyolefin, or a polycarbonate. The surface 120 may comprise a portion of a container used for the storage or delivery of a medicant, such as a syringe, a cartridge barrel, a vial, and the like, as well as plungers and seals used on or with these containers.

Various embodiments may also comprise the use of a coupling agent applied to the surface 120. The coupling agent may comprise a silane coupling agent. Silane coupling agents may have the ability to form a bond between organic materials and inorganic materials such as materials with siliceous properties (e.g., glass).

The general chemical structure of a silane coupling agent is R—$(CH_2)_n$—Si—$X_3$. This structure illustrates the two classes of functionality typical to coupling agents. The R group may be a nonhydrolyzable organofunctional group linked to the silicon atom via a silicon-carbon bond. The functionality of the R group may be selected to impart desired characteristics, such as increasing the hydrophobic property of the inorganic surface or provide the ability to bond with an organic polymer. The X group may be a hydrolyzable group capable of forming silanol groups (Si—OH). Silanol groups may bond with hydroxyl groups on ceramic surfaces such as siliceous materials. The hydrolyzable groups may be halogens, alkoxy (—O—R), or acyloxy (—O—COR). Each of these groups may be capable of reacting with water to form silanols that in turn may condense to form siloxane linkages or react with hydroxyl groups on ceramic surfaces.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising", and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

EXAMPLES

Example 1

Figure 6:
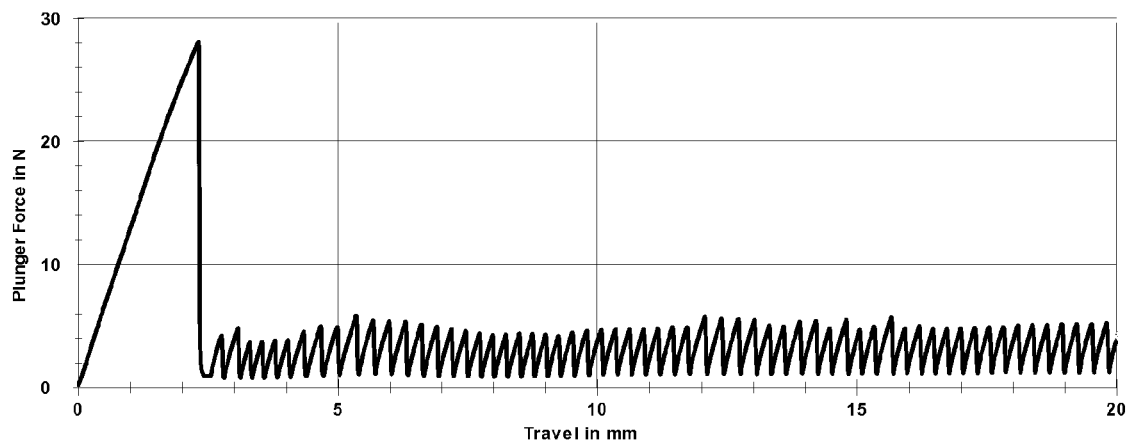
FIG. 6 is a plot of experimental measurements of the force applied to a syringe plunger as a function of plunger travel distance, where the syringe barrel was coated with a specific lubricant and was not exposed to any post-treatment.
Figure 7:
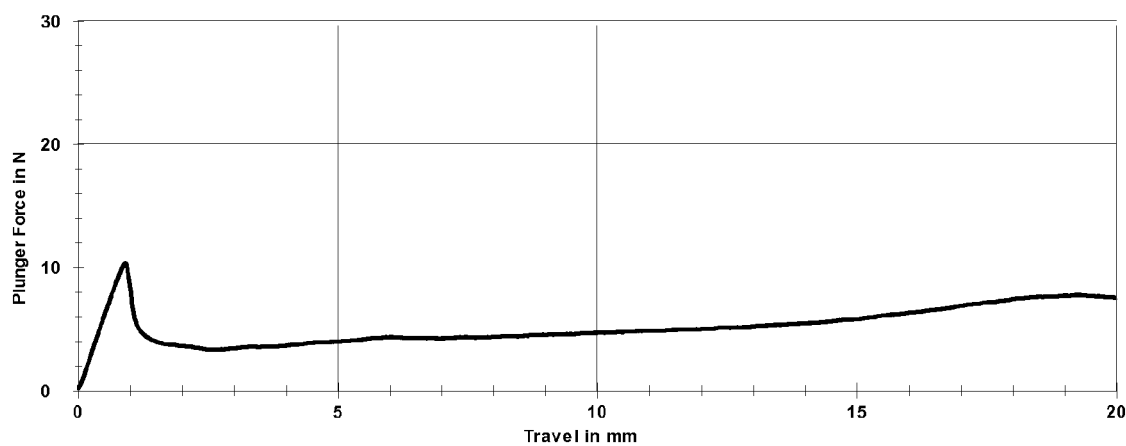
FIG. 7 is a plot of experimental measurements of the force applied to a syringe plunger as a function of plunger travel distance, where the syringe barrel was coated with a specific lubricant and subsequently exposed to a direct plasma treatment.
Figure 8:
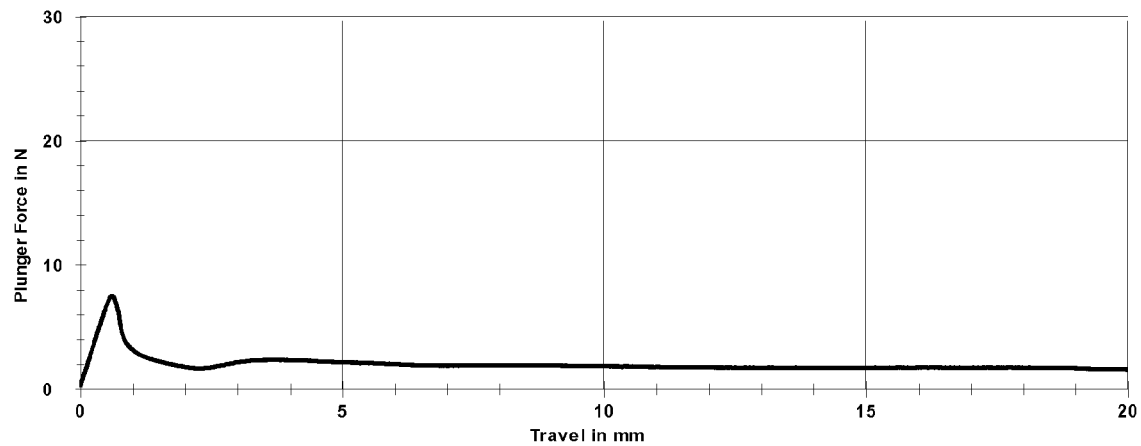
FIG. 8 is a plot of experimental measurements of the force applied to a syringe plunger as a function of plunger travel distance, where the syringe barrel was coated with a specific lubricant and subsequently exposed to a downstream plasma treatment.
Figure 9:
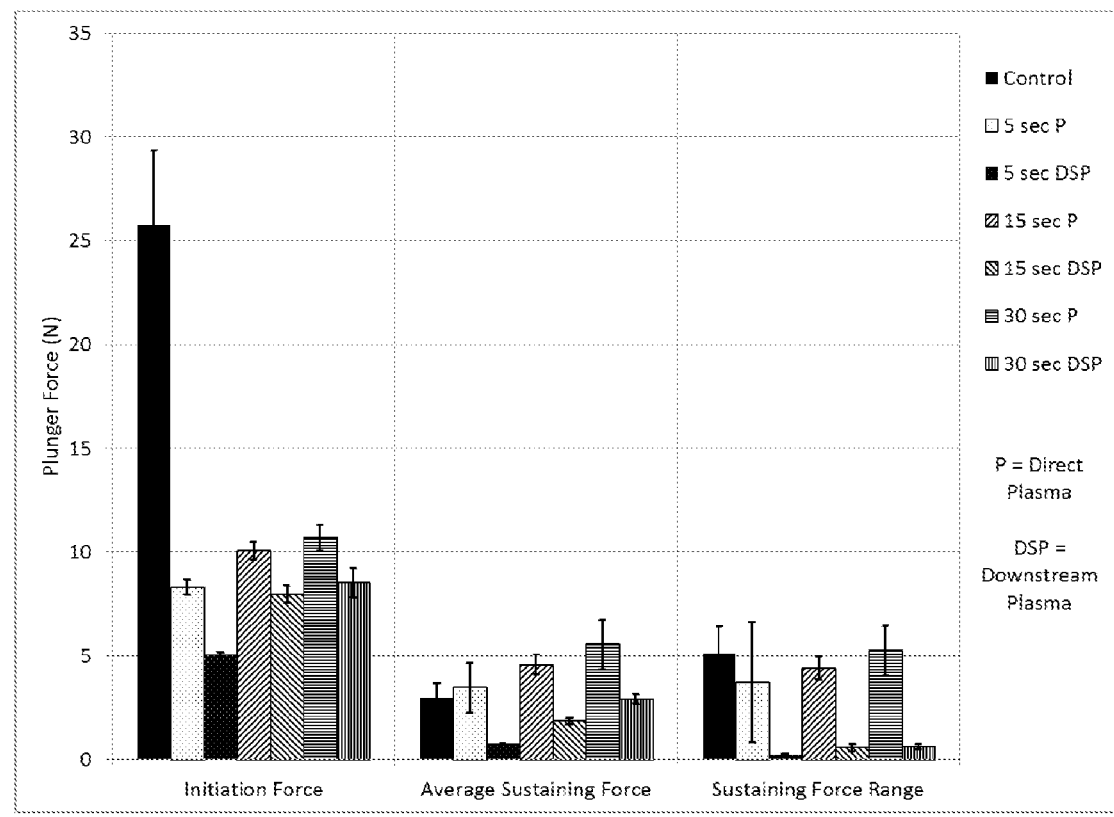
FIG. 9 is a summary plot of experimental measurements of the force applied to a syringe plunger as a function of plunger travel distance, where the syringe barrel was coated with a specific lubricant and subsequently either exposed to a post-treatment process or not exposed to any post-treatment.

Non-lubricated injection molded 3 cc cyclic olefin polymer syringe barrels were sprayed with 0.45 µL of 1,000 cSt polydimethylsiloxane (silicone) oil to achieve a thin layer of lubricant on the inside surface of the syringe. The inner cavities were then exposed to a downstream argon plasma, a direct argon plasma, or no plasma treatment. The duration of the downstream or direct plasma treatments were 5, 15, and 30 seconds. The syringe barrels were assembled with plungers and stored overnight at room temperature. After storage, the assembled syringes were mounted onto a force measurement apparatus for testing. The force required to push the plunger down the barrel at an infusion rate of 5 mm/min is shown in FIGS. 6 through 9. FIG. 6 displays the force curve of a silicone lubricated syringe that was not plasma treated. The initiation force for this syringe was high and there was chatter or "stick-slip" in the sustaining force region. FIGS. 7 and 8 display the force curves for syringes treated with 15 seconds of direct and downstream plasma respectively. Both treatment processes reduced the initiation force and the stick-slip chatter. Additionally, the forces for the downstream plasma were lower than those for direct plasma treatment. A summary of all force curves is provided in FIG. 9. In all cases, the plasma and downstream plasma treatments were superior to the untreated syringe. For every treatment time, the downstream plasma resulted in superior force characteristics compared to direct plasma treatment and to no plasma treatment.

Example 2

Figure 10:
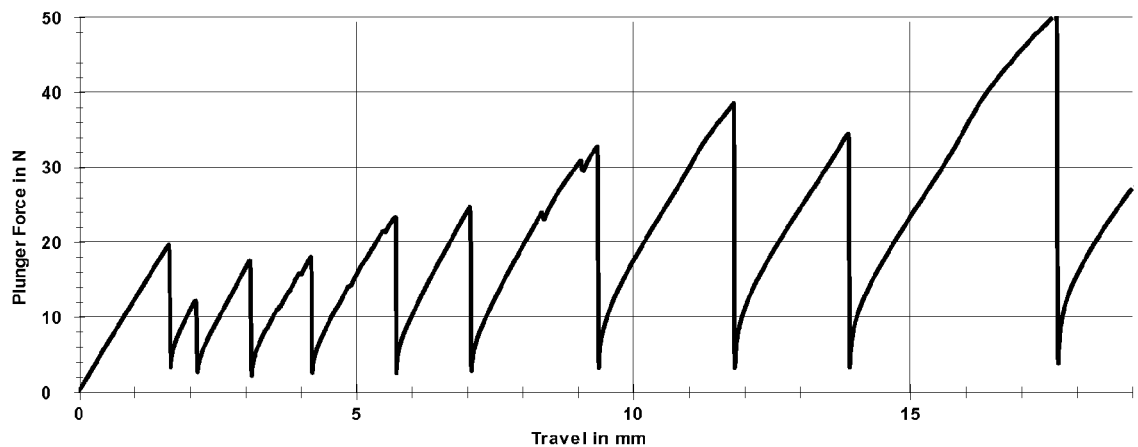
FIG. 10 is a plot of experimental measurements of the force applied to a syringe plunger as a function of plunger travel distance, where the syringe barrel was coated with a specific lubricant and was not exposed to any post-treatment.
Figure 11:
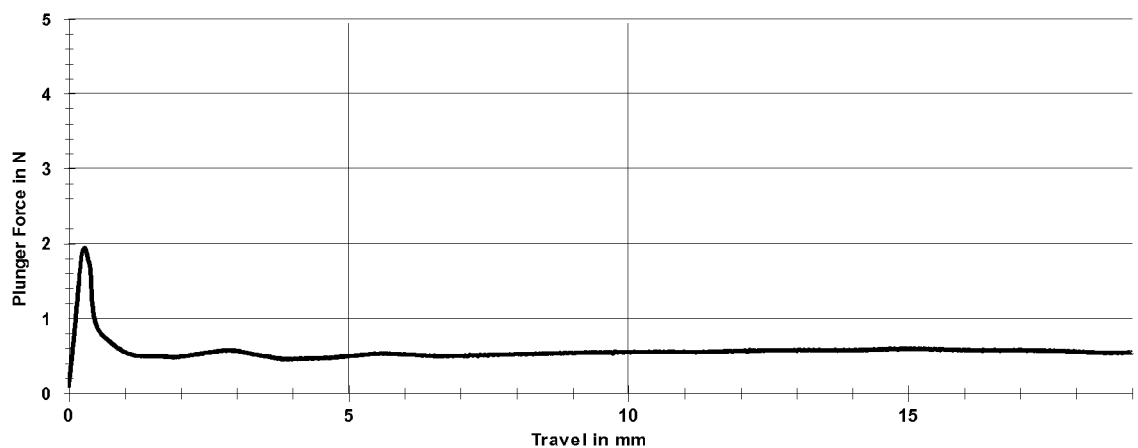
FIG. 11 is a plot of experimental measurements of the force applied to a syringe plunger as a function of plunger travel distance, where the syringe barrel was coated with a specific lubricant and subsequently exposed to a downstream plasma treatment.

Non-lubricated injection molded 3 cc cyclic olefin polymer syringe barrels were sprayed with 0.45 µL of M60 perfluoropolyether oil to achieve a thin layer of lubricant on the inside surface of the syringe. The inner cavities were then exposed to a downstream argon plasma for 3 minutes or no plasma treatment. The syringe barrels were assembled with plungers and stored overnight at room temperature. After storage, the assembled syringes were mounted onto a force measurement apparatus for testing. The force required to push the plunger down the barrel at an infusion rate of 5 mm/min is shown in FIGS. 10 and 11. FIG. 10 displays the force curve of a perfluoropolyether lubricated syringe that was not processed with the downstream plasma treatment process. The initiation force for this syringe was high and there is stick-slip chatter throughout the syringe. FIG. 11 displays the force curve for syringes treated with 3 minutes downstream plasma. The downstream plasma significantly reduced the plunger force and eliminated the stick-slip chatter.

Example 3

Prophetic Example

Energized gaseous species can be formed by flowing a gas over a catalytic surface. Some examples of catalytic surfaces include, but are not limited to, a heated platinum wire or mesh, a heated tungsten wire, or nanoparticles of noble metals. These surfaces can break the bonds of different molecules or excite atoms to form free radicals. By exposing a lubricated surface to a flux of these energized species, crosslinking may occur. Therefore, a similar result of reducing stiction in a lubricated syringe is expected when the lubricated syringe is exposed to an energize species rich gas stream that is produced on a catalytic surface.

Example 4

Prophetic Example

Energized gaseous species can be formed by intense photonic sources such as a flash lamp emitting visible or UV radiation. By exposing a lubricated surface to a flux of these energized species, cross-linking may occur. Therefore, a similar result of reducing stiction in a lubricated syringe is expected when the lubricated syringe is exposed to an energize species rich gas stream that is produced on a catalytic surface.

What is claimed is:

1. A method for treating a lubricant on a surface, comprising:
    introducing a gas stream into an activation zone;
    generating one or more energized gaseous species in the activation zone;
    moving at least a portion of the gas stream and energized gaseous species apart from the activation zone;
    separating at least a portion of any charged species generated in the activation zone from the gas stream and retaining at least a portion of any uncharged energized gaseous species in the gas stream;
    directing the gas stream and retained energized gaseous species in proximity to a lubricant on a surface; and
    allowing the gas stream and retained energized gaseous species to react with the lubricant, thereby altering the material properties of at least a portion of the lubricant.

2. The method of claim 1, wherein the retained energized gaseous species comprise excited noble gas atoms.

3. The method of claim 1, wherein the energized gaseous species comprise free radicals.

4. The method of claim 3, wherein the free radicals comprise reactive gas atoms.

5. The method of claim 1, wherein generating one or more energized gaseous species comprises generating a plasma within the activation zone within a chamber.

6. The method of claim 5, further comprising maintaining a pressure at the activation zone within the chamber of near atmospheric pressure.

7. The method of claim 6, wherein the pressure at the activation zone within the chamber is about 760 torr.

8. The method of claim 5, further comprising maintaining a vacuum at the activation zone within the chamber.

9. The method of claim 8, wherein the pressure at the activation zone within the chamber is less than 200 torr.

10. The method of claim 1, wherein the step of separating at least a portion of any charged species from the gas stream and retaining at least a portion of any uncharged energized gaseous species comprises providing an electrical ground to separate the charged species from the uncharged energized gaseous species.

11. The method of claim 1, wherein the step of separating at least a portion of any charged species from the gas stream and retaining at least a portion of any uncharged energized gaseous species comprises providing an electrostatic or electromagnetic field to separate the charged species from the uncharged energized gaseous species.

12. The method of claim 1, wherein the step of allowing the gas stream and retained energized gaseous species to react with the lubricant occurs in a treatment zone.

13. The method of claim 12, wherein the treatment zone is spaced apart from the activation zone by a transfer zone.

14. The method of claim 13, wherein the step of separating at least a portion of any charged species generated in the activation zone from the gas steam and retaining at least a portion of any uncharged energized species in the gas stream comprises neutralizing at least a portion of any charged species in the gas stream through a process of recombination that occurs in the transfer zone.

15. The method of claim 1, wherein the gas stream comprises one or more gases.

16. The method of claim 1, further comprising applying a coupling agent to the surface prior to applying a lubricant.

17. The method of claim 16, wherein the coupling agent is a silane coupling agent.

18. The method of claim 17, wherein the silane coupling agent has the general formula R—$(CH_2)_n$—Si—$X_3$, where R comprises a nonhydrolyzable group, X comprises a hydrolysable group, and n is an integer.

19. The method of claim 1, wherein the surface is a polymer surface.

20. The method of claim 19, wherein the polymer surface is a cyclic olefin polymer.

21. The method of claim 19, wherein the polymer surface is a cyclic olefin copolymer.

22. The method of claim 19, wherein the polymer surface is a polyolefin.

23. The method of claim 19, wherein the polymer surface is a polycarbonate surface.

24. The method of claim 1, wherein the surface is a glass surface.

25. The method of claim 1, wherein the surface is a container for storage of a medicant.

26. The method of claim 1, wherein the surface is a container used for delivery of a medicant into or onto a human or animal.

27. The method of claim 1, wherein the surface is a syringe or cartridge barrel.

28. The method of claim 1, wherein the lubricant is a polysiloxane material, a perfluoropolyether material, a functionalized polysiloxane material, a functionalized perfluoropolyether material, or mixtures thereof.

29. The method of claim 28, wherein the polysiloxane material is a polydimethyl siloxane.

30. The method of claim 1, wherein altering the material properties of at least a portion of the lubricant comprises at least partially immobilizing the lubricant.

31. The method of claim 30, wherein immobilizing the lubricant comprises reducing migration of lubricant particulates into a liquid in contact with the lubricant.

32. The method of claim 31, wherein the lubricant particulates comprise visible and subvisible particulates.

33. The method of claim 1, wherein altering the material properties of at least a portion of the lubricant comprises altering a frictional force between a second surface in sliding contact with the lubricant on the surface.

34. A method for treating a lubricant on a surface, comprising:
   introducing a gas stream comprising one or more gases into an activation zone;
   generating a mixture of uncharged energized gaseous species and charged species in the activation zone;
   moving at least a portion of the mixture apart from the activation zone;
   separating at least a portion of the charged species from the mixture, creating an uncharged energized gaseous species-rich gas stream;
   directing the uncharged energized gaseous species-rich gas stream in proximity to the lubricant; and
   allowing the uncharged energized gaseous species-rich gas stream to react with the lubricant, thereby altering the material properties of at least a portion of the lubricant.

35. The method of claim 34, wherein the uncharged energized gaseous species comprise free radicals.

36. The method of claim 34, wherein the step of separating at least a portion of the charged species from the mixture comprises providing an electrical ground to separate the charged species from the mixture.

37. The method of claim 34, wherein the step of separating at least a portion of the charged species from the mixture comprises providing an electrostatic field to separate the charged species from the mixture.

38. The method of claim 34, wherein the step of allowing the uncharged energized gaseous species-rich gas stream to react with the lubricant occurs in a treatment zone.

39. The method of claim 38, wherein the treatment zone is spaced apart from the activation zone by a transfer zone.

40. The method of claim 39, wherein the step of separating at least a portion of any charged species generated in the activation zone from the mixture and creating the uncharged energized gaseous species-rich gas stream comprises neutralizing at least a portion of any charged species in the mixture through a process of recombination.

41. The method of claim 34, wherein altering the material properties of at least a portion of the lubricant comprises at least partially immobilizing the lubricant.

42. The method of claim 41, wherein immobilizing the lubricant comprises reducing migration of lubricant particulates into a liquid in contact with the lubricant.

43. The method of claim 42, wherein the lubricant particulates comprise visible and subvisible particulates.

44. The method of claim 34, wherein altering the material properties of at least a portion of the lubricant comprises altering a frictional force between a second surface in sliding contact with the lubricant on the surface.

45. A method for treating a lubricant on a surface, comprising:
   introducing a gas stream into an activation zone;
   generating one or more energized gaseous species in the activation zone;
   moving at least a portion of the gas stream and energized gaseous species apart from the activation zone;
   causing at least a portion of any charged species in the gas stream to react with one another to form neutral species;
   separating at least a portion of any remaining charged species from the gas stream and retaining at least a portion of any uncharged energized gaseous species in the gas stream;
   directing the gas stream and retained energized gaseous species in proximity to a lubricant on a surface; and
   allowing the gas stream and retained energized gaseous species to react with the lubricant, thereby altering the material properties of at least a portion of the lubricant.

46. The method of claim 45, wherein altering the material properties of at least a portion of the lubricant comprises at least partially immobilizing the lubricant.

47. The method of claim 46, wherein immobilizing the lubricant comprises reducing migration of lubricant particulates into a liquid in contact with the lubricant.

48. The method of claim 47, wherein the particulates comprise visible and subvisible particulates.

49. The method of claim 45, wherein altering the material properties of at least a portion of the lubricant comprises altering a frictional force between a second surface in sliding contact with the lubricant on the surface.

* * * * *